(12) United States Patent
Smead et al.

(10) Patent No.: US 11,944,773 B2
(45) Date of Patent: Apr. 2, 2024

(54) TATTOO MACHINE RECHARGEABLE BATTERY UNIT WITH VOLTAGE CONTROLLER

(71) Applicant: FK Irons Inc., Doral, FL (US)

(72) Inventors: Robert Smead, Goshen, IN (US); Christopher Sanford, Las Vegas, NV (US); Dahao Xuan, Brooklyn, NY (US)

(73) Assignee: FK Irons Inc., Doral, FL (US)

( * ) Notice: Subject to any disclaimer, the term of this patent is extended or adjusted under 35 U.S.C. 154(b) by 0 days.

(21) Appl. No.: 18/087,369

(22) Filed: Dec. 22, 2022

(65) Prior Publication Data

US 2023/0130433 A1 Apr. 27, 2023

Related U.S. Application Data

(63) Continuation of application No. 17/954,226, filed on Sep. 27, 2022, now Pat. No. 11,559,675, which is a continuation of application No. 17/843,695, filed on Jun. 17, 2022, now Pat. No. 11,471,658, which is a continuation of application No. 16/823,900, filed on Mar. 19, 2020, now Pat. No. 11,406,807.

(Continued)

(51) Int. Cl.
*H02J 7/00* (2006.01)
*A61M 37/00* (2006.01)

(52) U.S. Cl.
CPC ....... *A61M 37/0076* (2013.01); *H02J 7/0045* (2013.01); *H02J 7/0047* (2013.01); *H02J 7/0063* (2013.01); *A61M 2205/33* (2013.01); *A61M 2205/505* (2013.01); *A61M 2205/8206* (2013.01); *A61M 2209/082* (2013.01); *A61M 2210/04* (2013.01)

(58) Field of Classification Search
CPC .............................. H02J 7/00; A61M 37/0076
See application file for complete search history.

(56) References Cited

U.S. PATENT DOCUMENTS

| 2,588,623 A | 3/1952 | Eliscu |
| D226,829 S | 5/1973 | Staub |

(Continued)

FOREIGN PATENT DOCUMENTS

| CN | 2800622 Y | 7/2006 |
| CN | 102469867 | 5/2012 |

(Continued)

OTHER PUBLICATIONS

Chinese Office Action dated Apr. 26, 2023 in Chinese Application No. 202080002370.2, with translation.

(Continued)

*Primary Examiner* — Robert Grant
(74) *Attorney, Agent, or Firm* — Akerman LLP; Peter A. Chiabotti

(57) ABSTRACT

A compact battery and voltage supply controller apparatus for a tattoo machine is disclosed. The battery and controller are configured to connect the battery to the tattoo machine through replaceable internally received magnetic connection adapters. The toggle switch operated display screen provides easy-to-view status and health of the battery and incremental voltage adjustment using a voltage boost circuit and adjustment knob. The internal battery can be replaced and/or removed and recharged.

20 Claims, 12 Drawing Sheets

Related U.S. Application Data

(60) Provisional application No. 62/825,020, filed on Mar. 27, 2019.

(56) References Cited

U.S. PATENT DOCUMENTS

| | | |
|---|---|---|
| D229,869 S | 1/1974 | Staub |
| D241,475 S | 9/1976 | Staub |
| D254,150 S | 2/1980 | Barton |
| D288,359 S | 2/1987 | Hoff |
| 4,647,260 A | 3/1987 | O'Hara |
| D294,388 S | 2/1988 | Hardy |
| D294,519 S | 3/1988 | Hardy |
| 5,032,043 A | 7/1991 | Hollifield |
| 5,279,552 A | 1/1994 | Magnet |
| 5,341,704 A | 8/1994 | Klemm |
| 5,380,132 A | 1/1995 | Parks |
| D364,923 S | 12/1995 | Chou |
| 5,586,473 A | 12/1996 | Chou |
| 5,601,387 A | 2/1997 | Sanford |
| D380,046 S | 6/1997 | Domanowski |
| D389,578 S | 1/1998 | Emerson |
| D389,915 S | 1/1998 | Emerson |
| D433,752 S | 11/2000 | Saravia |
| D434,149 S | 11/2000 | Mirhashemi |
| D439,337 S | 3/2001 | Jones |
| D440,310 S | 4/2001 | Laks |
| D448,483 S | 9/2001 | Behnke |
| D453,833 S | 2/2002 | Hess |
| 6,345,553 B1 | 2/2002 | Adler et al. |
| D457,955 S | 5/2002 | Bilitz |
| D465,279 S | 11/2002 | Etter |
| 6,505,530 B2 | 1/2003 | Adler |
| D490,152 S | 5/2004 | Myall |
| D493,530 S | 7/2004 | Reschke |
| D493,532 S | 7/2004 | Levaughn |
| 6,772,656 B2 | 8/2004 | Godoy |
| D521,641 S | 5/2006 | Reschke |
| D535,396 S | 1/2007 | Reschke |
| D536,451 S | 2/2007 | Haydu |
| D538,934 S | 3/2007 | Wilkinson |
| D538,936 S | 3/2007 | Bohmel |
| 7,211,097 B2 | 5/2007 | Carrasco |
| 7,225,708 B2 | 6/2007 | Chen |
| D549,325 S | 8/2007 | Schnitzler |
| D549,779 S | 8/2007 | Shimizu |
| D560,803 S | 1/2008 | Tasse |
| 7,335,211 B2 | 2/2008 | Chen |
| 7,337,697 B2 | 3/2008 | Badar |
| D575,343 S | 8/2008 | Cetera |
| D581,530 S | 11/2008 | Thierfelder |
| D582,981 S | 12/2008 | Bhavnani |
| D586,465 S | 2/2009 | Faulkner |
| D597,668 S | 8/2009 | Woodruff |
| D612,051 S | 3/2010 | Ruf |
| D621,042 S | 8/2010 | Ruf |
| D622,000 S | 8/2010 | Kluge |
| 7,810,414 B2 | 10/2010 | Hsu |
| D628,293 S | 11/2010 | Ruf |
| D628,695 S | 12/2010 | Ruf |
| D634,426 S | 3/2011 | Zollers |
| D638,939 S | 5/2011 | Eikhoff |
| D645,965 S | 9/2011 | Muto |
| 8,029,527 B2 | 10/2011 | Lisec |
| D664,657 S | 7/2012 | Vieira |
| D667,554 S | 9/2012 | Casabonne |
| D677,790 S | 3/2013 | Little |
| D679,396 S | 4/2013 | Jan |
| 8,414,531 B2 | 4/2013 | Oginski |
| D691,263 S | 10/2013 | Chen |
| 8,794,109 B2 | 8/2014 | Lee |
| 8,920,379 B2 | 12/2014 | Lee |
| D723,685 S | 3/2015 | Myers |
| 9,050,445 B2 | 6/2015 | Klebs |
| D736,915 S | 8/2015 | Schultz |
| D737,441 S | 8/2015 | Presser |
| D737,972 S | 9/2015 | Chen |
| 9,126,027 B2 | 9/2015 | Lin |
| D743,546 S | 11/2015 | Jayaraj |
| D745,152 S | 12/2015 | Mayer |
| D750,243 S | 2/2016 | Tetzlaff |
| D750,258 S | 2/2016 | Crossley |
| 9,259,561 B2 | 2/2016 | Lee |
| D762,303 S | 7/2016 | Jayaraj |
| 9,393,395 B2 | 7/2016 | Miller |
| D763,443 S | 8/2016 | Chen |
| D765,841 S | 9/2016 | Schuerg |
| D765,842 S | 9/2016 | Schuerg |
| D766,432 S | 9/2016 | Schuerg |
| D779,670 S | 2/2017 | Krystyniak |
| D781,419 S | 3/2017 | Bojanowski |
| D782,041 S | 3/2017 | Pell |
| D782,667 S | 3/2017 | Fuhr |
| D785,795 S | 5/2017 | Amano |
| D791,946 S | 7/2017 | Schwartz |
| D791,947 S | 7/2017 | Chen |
| 9,707,385 B1 | 7/2017 | Chen |
| D794,192 S | 8/2017 | Schuerg |
| D794,193 S | 8/2017 | Schuerg |
| D794,194 S | 8/2017 | Schuerg |
| D803,398 S | 11/2017 | Israni |
| D805,195 S | 12/2017 | Lee |
| D805,196 S | 12/2017 | Lee |
| D805,197 S | 12/2017 | Lee |
| D805,198 S | 12/2017 | Lee |
| D805,640 S | 12/2017 | Lee |
| D815,738 S | 4/2018 | Ye |
| D819,207 S | 5/2018 | Blank |
| D831,208 S | 10/2018 | Benisty |
| D837,371 S | 1/2019 | Zu |
| D837,372 S | 1/2019 | Zu |
| D839,425 S | 1/2019 | Zanata |
| 10,439,411 B2 | 10/2019 | Narayanasamy |
| 10,449,346 B2 | 10/2019 | Juan |
| 10,471,246 B1 | 11/2019 | Lipscomb |
| 2005/0055042 A1 | 3/2005 | Carrasco |
| 2006/0020283 A1 | 1/2006 | Lisec |
| 2008/0287978 A1 | 11/2008 | Hickman |
| 2010/0036317 A1 | 2/2010 | Oginski |
| 2010/0241151 A1 | 9/2010 | Rickard |
| 2011/0048174 A1 | 3/2011 | Lin |
| 2011/0288575 A1* | 11/2011 | Colton .............. A61M 37/0076 606/185 |
| 2012/0123462 A1 | 5/2012 | Lee |
| 2012/0179134 A1 | 7/2012 | Garitano |
| 2014/0358172 A1 | 12/2014 | Lin |
| 2014/0358173 A1 | 12/2014 | Lin |
| 2015/0202420 A1 | 7/2015 | Miller |
| 2016/0038176 A1 | 2/2016 | Smith |
| 2016/0354592 A1 | 12/2016 | Juan |
| 2017/0014609 A1 | 1/2017 | Spadon, III |
| 2017/0072177 A1 | 3/2017 | Oscar |
| 2017/0157382 A1 | 6/2017 | Siciliano |
| 2017/0317444 A1 | 11/2017 | Narayanasamy et al. |
| 2018/0043146 A1 | 2/2018 | Vescovi |
| 2018/0056054 A1 | 3/2018 | Siciliano |
| 2018/0289902 A1 | 10/2018 | Xiang |
| 2018/0360487 A1 | 12/2018 | Algeri |
| 2018/0369553 A1 | 12/2018 | Siciliano |
| 2019/0134371 A1 | 5/2019 | Johansson |

FOREIGN PATENT DOCUMENTS

| | | |
|---|---|---|
| CN | 102812612 A | 12/2012 |
| CN | 203790439 | 8/2014 |
| CN | 207442503 U | 6/2018 |
| EP | 2944349 | 11/2015 |
| KR | 100973628 | 8/2010 |
| KR | 20150009459 | 1/2015 |
| RU | 2270040 | 2/2006 |
| WO | 2010120111 | 10/2010 |
| WO | 2014202055 | 12/2014 |
| WO | 2015094041 | 6/2015 |
| WO | 2015160370 | 10/2015 |
| WO | WO2015156715 A1 | 10/2015 |

(56) References Cited

FOREIGN PATENT DOCUMENTS

| WO | 2016159465 | 10/2016 |
| WO | 2017189606 | 11/2017 |
| WO | WO2017189606 A1 | 11/2017 |

OTHER PUBLICATIONS

Chinese Office Action dated Jan. 16, 2024 in Chinese Application No. 202080002370.2, with translation.

* cited by examiner

TATTOO MACHINE RECHARGEABLE BATTERY UNIT WITH VOLTAGE CONTROLLER This application is a continuation of U.S. patent application Ser. No. 17/954,226, filed Sep. 27, 2022, which is a continuation of U.S. patent application Ser. No. 17/843,695, filed Jun. 17, 2022, now U.S. Pat. No. 11,471,658, which is a continuation of U.S. patent application Ser. No. 16/823,900, filed Mar. 19, 2020, now U.S. Pat. No. 11,406,807, which claims the benefit of prior filed provisional application Ser. No. 62825020, filed Mar. 27, 2019, the entirety of all of which is incorporated herein by reference.

FIELD OF APPLICATION

This patent application is directed to a rechargeable battery system for powering tattoo machines. More particularly, this application is directed to a compact, rechargeable battery system with a voltage controller and variable mounting configurations for use with tattoo machines.

BACKGROUND

Tattoo machines are conventionally powered by a mains supply, which typically involves a long cord. Tattoo machines can also be found using a battery as the power supply wherein the battery is affixed (tied) to the artist's arm with a power cable extending to the machine. In many instances, the prior art's battery connection to the machine is insecure, prone to rotation during use, as well as possibly disconnecting. Additionally, the arm-attached battery can be cumbersome with the weight of the battery on the artist's arm being a source of irritation as well as effect the tattoo artist's dexterity and skill. This is especially so during a long tattooing session where the battery may become warm. Rechargeable batteries, with "speed" control, for tattoo machines do exist, but the execution of the machine often results in inaccurate power control, not suitable for brushless DC motors, and an awkward cumbersome battery "pendulum" weighting on the end of the machine making precise control of the opposite, tattooing, end more difficult.

What is desired in the art is a compact lightweight rechargeable battery for a tattoo machine, with multiple adjustable tattoo machine to battery interface possibilities, to accommodate the artist's weighting and balance preferences, as well as providing easy-to-view status(es) of the battery health and voltage provision and adjustment modes.

SUMMARY

The present disclosure is a compact battery and voltage supply controller for a tattoo machine. The disclosure includes a battery system that allows the battery to direct-connect to the tattoo machine, through various internally received magnetic connection adapters, as well as providing easy-to-view status and health of the battery and incremental 0.01 V voltage adjustment using a voltage boost circuit or voltage modulator/potentiometer circuit actuated via a rotary adjustment knob.

DETAILED DESCRIPTION

Figure 1:
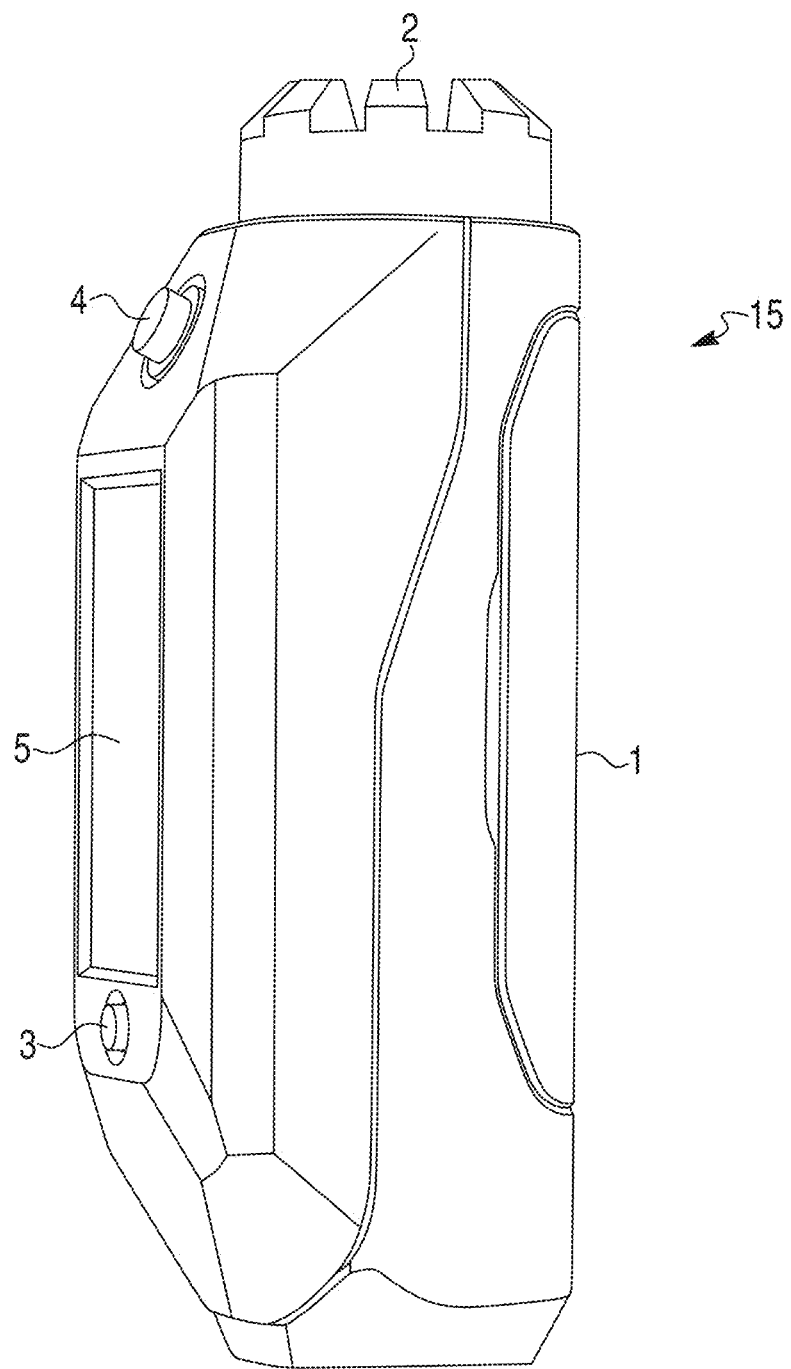
FIG. 1 shows a perspective view of a rechargeable battery and voltage control unit in accord with the present patent application.
Figure 2:
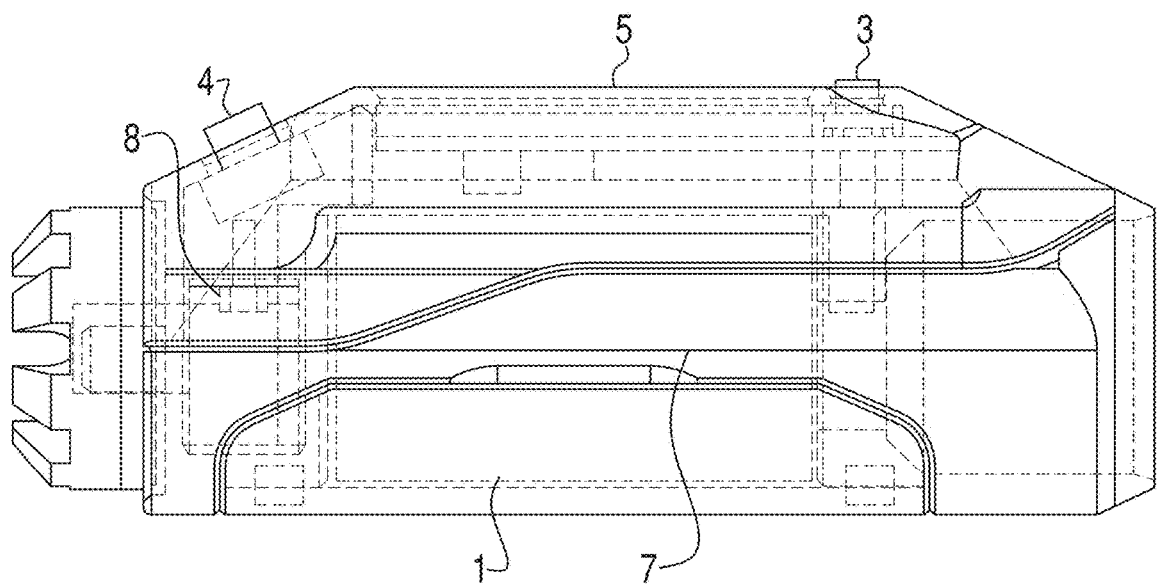
FIG. 2 shows a side, partial internal mechanism, view of the device in FIG. 1.
Figure 3:
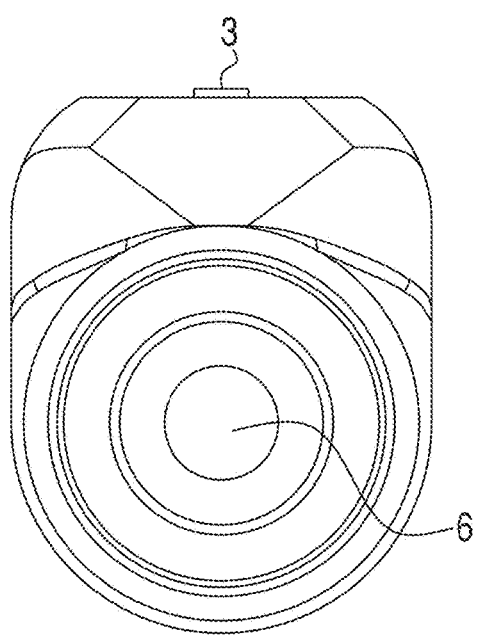
FIG. 3 shows a front view of the device in FIG. 1.
Figure 4:
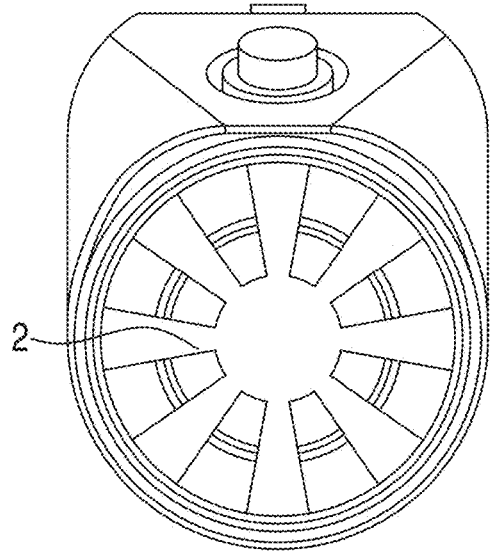
FIG. 4 shows a backend view of the device in FIG. 1.
Figure 5:
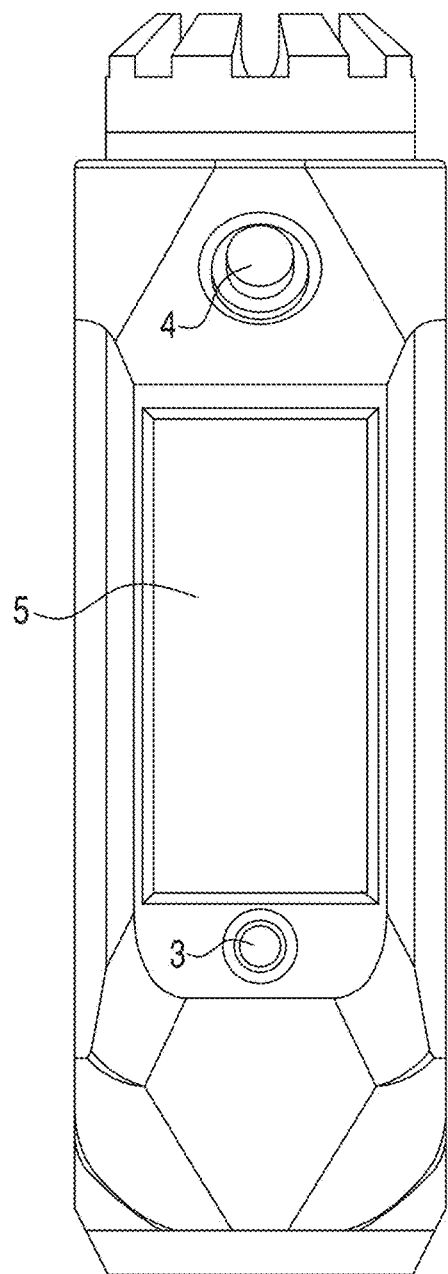
FIG. 5 shows a top plan view of the device in FIG. 1.
Figure 6:
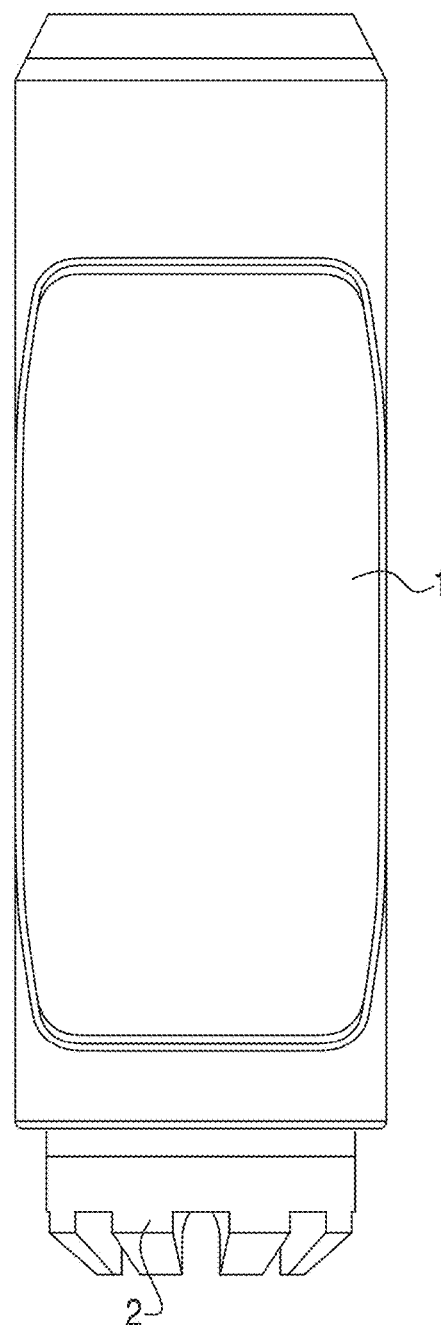
FIG. 6 shows a bottom plan view of the device in FIG. 1.
Figure 7:
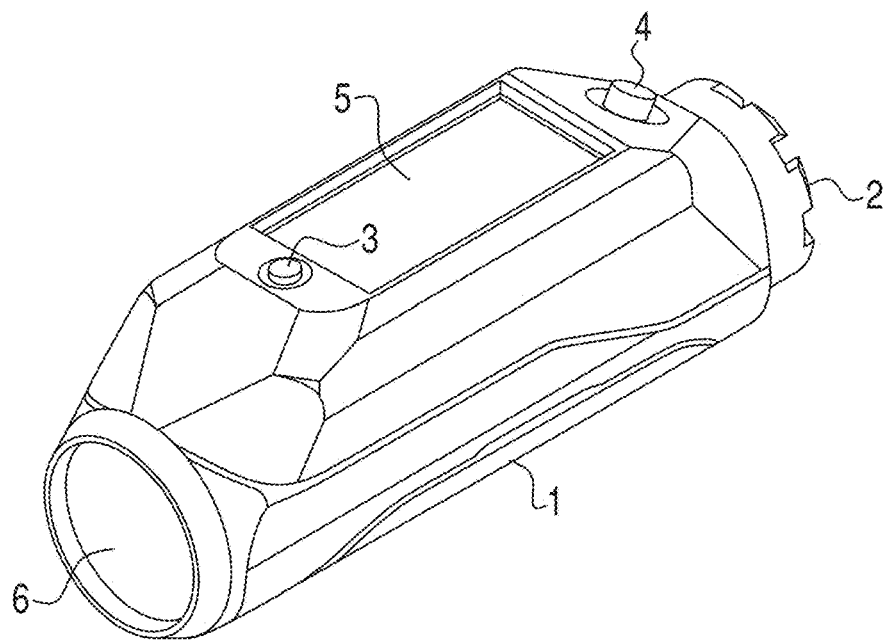
FIG. 7 shows a front ¾ view of the device in FIG. 1.

With respect to FIGS. 1-7: an exemplary compact battery power supply device in accord with the present disclosure is shown. The device includes a housing 15, display 5, power switch 4, adjustment knob 2, screen display toggle switch 3, battery compartment cover 1, and mounting face 6 with an insertion cavity for a magnetic type tattoo machine connector.

Figure 22:
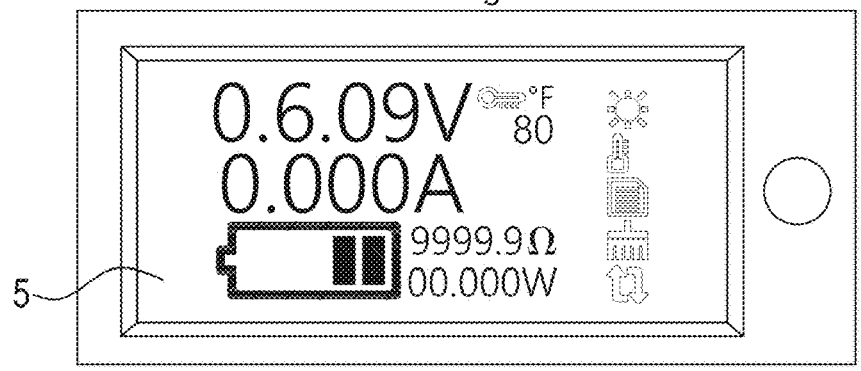
FIG. 22 is a screen shot of display 5 showing battery state, voltage, and temperature.
Figure 23:
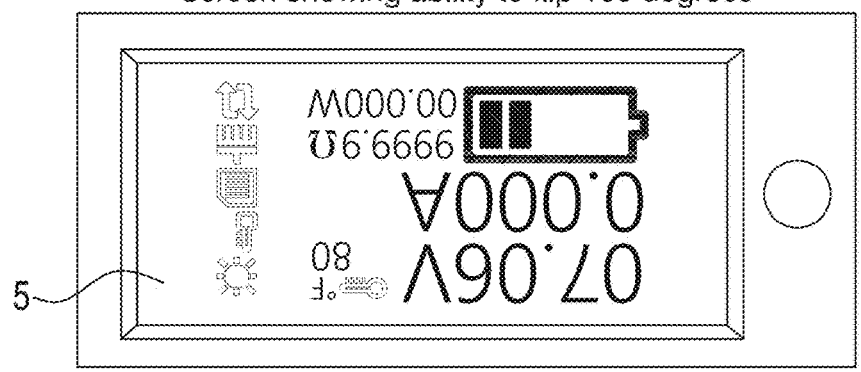
FIG. 23 is a screen shot of display 5 showing the supplied information flipped for left-handed users.
Figure 24:
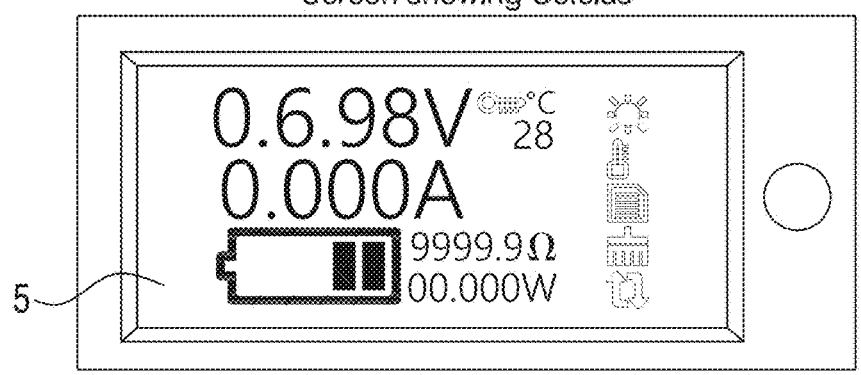
FIG. 24 is a screen shot of display 5 showing the same information as that in FIG. 22, but in metric units.

The display 5 can show any one or more of the following information to the artist: 1. Battery life (in time, volts, amps, percentage, etc.); 2. Temperature of the battery unit during operation; 3. Current draw; 4. Operational status (on/off/standby/charging/fully charged/etc.). See FIGS. 22-24. Of course, other information that may be useful, can also be shown, according to design preference. In some embodiments, the display 5 may be a touch sensitive display, allowing some degree of display and/or operational mode configurability. In the embodiment shown, control button 3 toggles the display screen between predetermined information register panels as well as flipping the screen for left and right-handed operational display. See FIG. 23.

In the embodiment shown, the screen toggle button 3 operates in the following sequence: Touch 1 turns on the MAIN SCREEN 5. Touch 2 allows the screen 5 to be turned off while the unit 15 still powers the machine. This gives the user the option to keep the screen off or on while in use. Touch 3 allows a user to switch the power supply temperature reading between Celsius and Fahrenheit. Touch 4 allows the user to store up to 2 preset voltages (whatever their optimal run speeds are for the task being undertaken). Touch 5 allows the user to clear the preset voltages they have stored. Touch 6 allows the user to flip the screen view 180 degrees. This is so the unit can be easily used by right or left-handed users and the screen is always facing the correct way for reading for a given user.

The power switch 4 is self-explanatory and switches the battery from an active to an inactive state. Adjustment knob 2 can be used to select different voltage/current settings in the battery between 0 and 12 volts in micro-adjustable increments of 0.01 volts through action of the shown rotary potentiometer 8, FIG. 2, or the boost circuit shown in FIG. 21.

Mounting face 6 provides a structure for the mounting magnetic connection interface adapters to mate the battery power supply unit 15 to a power end of a tattoo machine, or to any necessary adapter to configure a tattoo machine to interface with the internal magnetic connector 6 of device 15 shown. A tattoo machine selected for use is first equipped with the appropriate adapter, RCA, Phone, DC, clip cord, etc., then the device 15 is mated to the tattoo machine so equipped.

Figure 8:
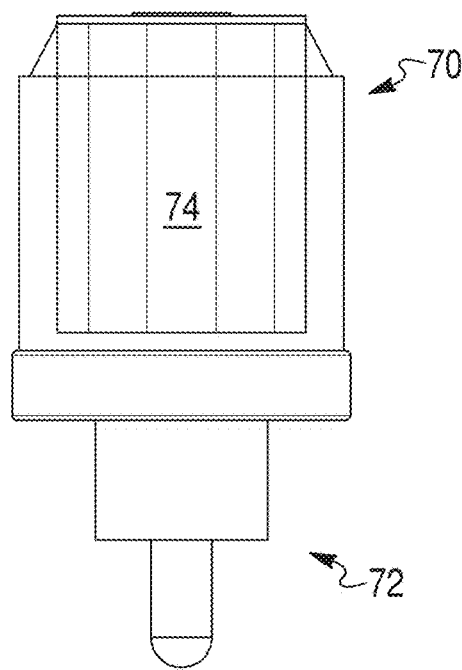
FIG. 8 shows an RCA type adapter for use with a tattoo machine having an RCA type power port.
Figure 12:
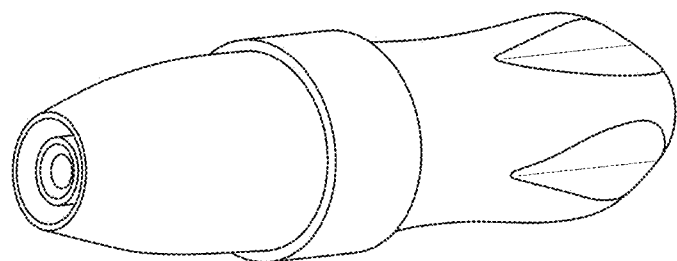
FIG. 12 show a power end of a tattoo machine having an RCA type power port on the end shown.
Figure 13:
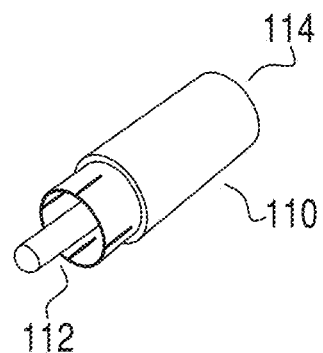
FIG. 13 shows a variation of the adapter shown in FIG. 8 above, i.e., an RCA adapter with an RCA male end and an opposite magnetic connection.

A Male RCA power connector 70, as shown in FIG. 8, has a male RCA end 72 opposite a magnetic style connector 74 that fits within the mounting face 6 of the battery supply housing 15 and makes contact with the magnetic electrical conductors within the mounting face 6. The Male RCA power connector 70 can be a removable "plug" and can be transferred to and from other tattoo machines equipped with an RCA type power and control interface. For example, the tattoo machine 50 shown in FIG. 12. The mounting face insertion cavity 6 provides a structural connection point for the power connector 70 to the battery system. That is, the mounting face 6 insertion cavity operates to physically "hold" power connector 70, which in turn physically attaches to the tattoo machine (not shown). The power connector 70 provides, in this example, both electrical connection and physical connection to the tattoo machine. In some embodiments, the electrical connection and physical connection capabilities may be accomplished through different structures.

Figure 9:
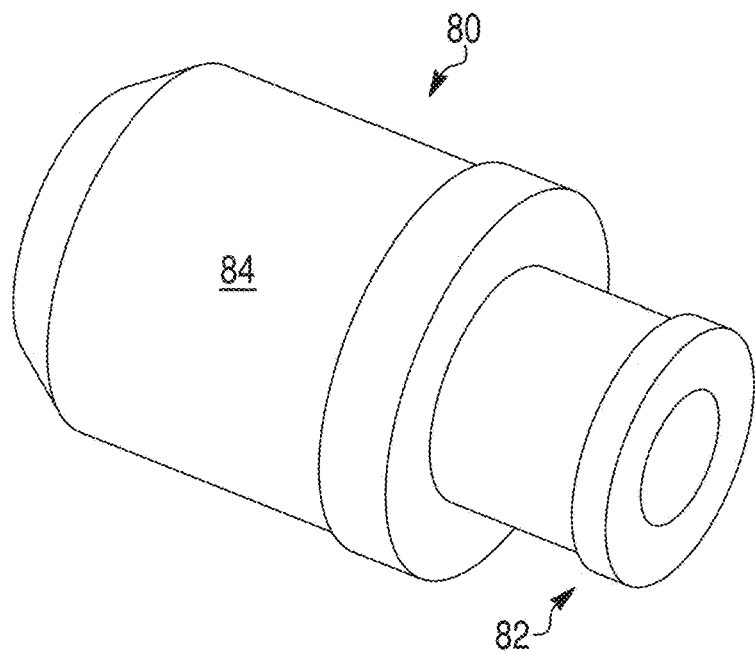
FIG. 9 shows a 3.5 mm phono type adaptor for use with a tattoo machine having a phono type power port.
Figure 14:
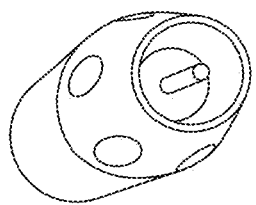
FIG. 14 shows the power end of a tattoo machine with a phono type power connector.
Figure 15:
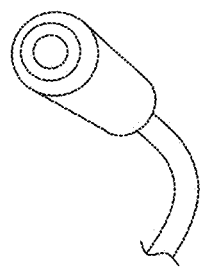
FIG. 15 shows a female 3.5 mm phono power receptacle.
Figure 16:
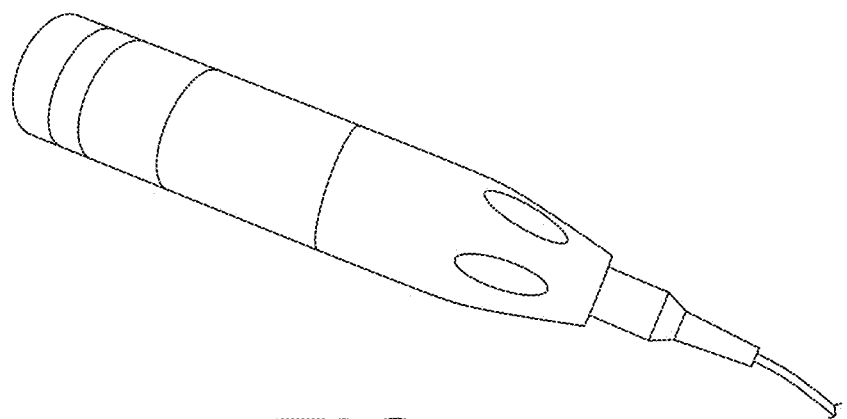
FIG. 16 shows a phono type power supply plugged into a tattoo machine having phono type power receptacle.

For example, in FIG. 9 an 3.5 mm phono power connector 80 is shown and has an extended female phono end 82 opposite a magnetic style connector 84 that fits within the mounting face 6 of the battery housing 15 and makes contact with the magnetic electrical conductors within the mounting face 6. The phono power connector 80 can be a removable "plug" and can be transferred to and from other tattoo machines equipped with a phono type power and control interface. For example, the tattoo machines 52 shown in FIG. 14, and 54 shown in FIG. 16. The mounting face insertion cavity 6 provides a structural connection point for the power connector 80 to the battery system. That is, the mounting face 6 insertion cavity operates to physically "hold" power connector 80, which in turn physically attaches to the tattoo machine (not shown). The power connector 80 provides, in this example, both electrical connection and physical connection to the tattoo machine.

Figure 10:
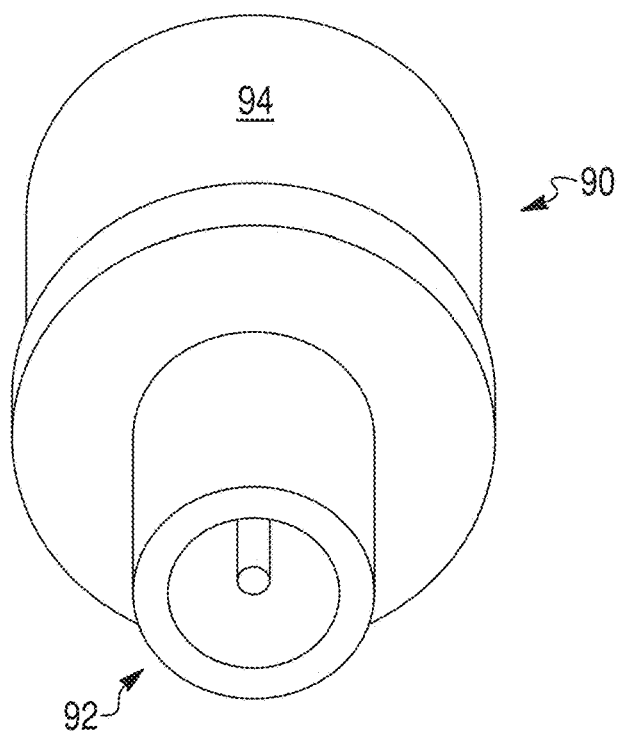
FIG. 10 shows an adapter for use with a tattoo machine having a typical DC connection port.

In another example, FIG. 10 shows a DC type adapter 90. The adapter 90 has a male DC end 92 opposite a magnetic style connector 94 that fits within the mounting face 6 of the battery housing 15 and makes contact with the magnetic electrical conductors within the mounting face 6. The male DC power connector 90 can be a removable "plug" and can be transferred to and from other tattoo machines equipped with an DC type power and control interface. The mounting face insertion cavity 6 provides a structural connection point for the power connector 90 to the battery system. That is, the mounting face 6 insertion cavity operates to physically "hold" power connector 90, which in turn physically attaches to the tattoo machine (not shown). The power connector 90 provides, in this example, both electrical connection and physical connection to the tattoo machine.

Figure 11:
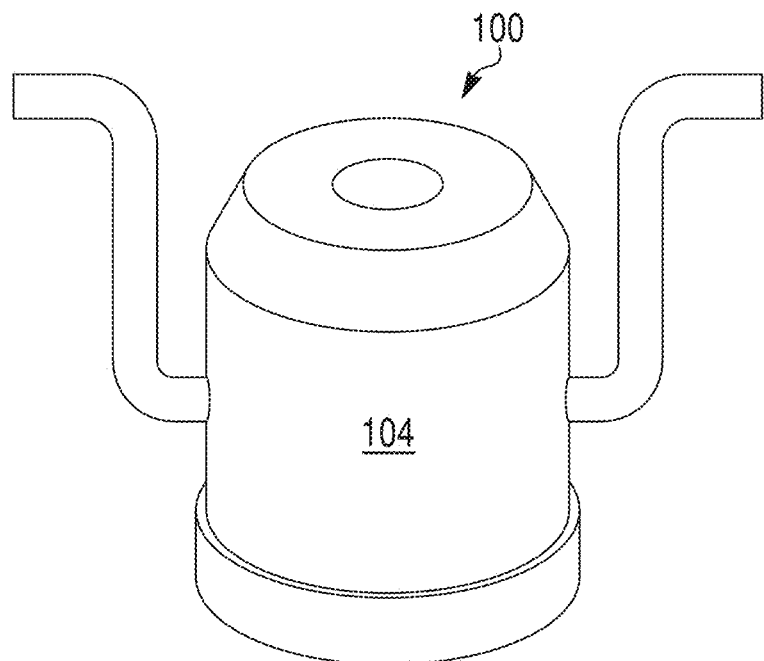
FIG. 11 shows an adapter for use with a "clip cord" type tattoo machine power supply.
Figure 17:
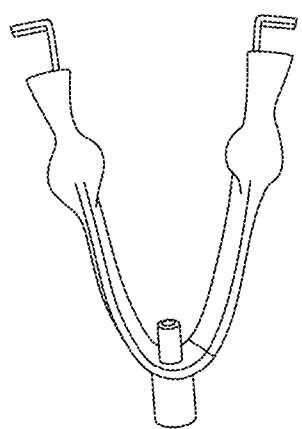
FIG. 17 shows a magnetic connector for a "clip cord" tattoo machine.
Figure 18:
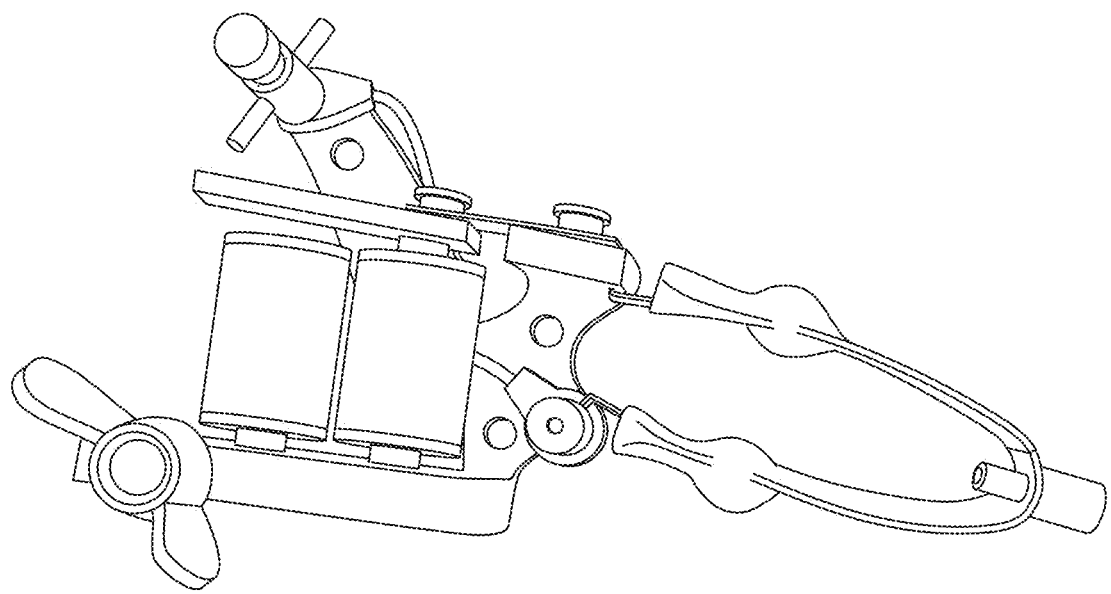
FIG. 18 shows the connector of FIG. 17 connected to a "clip cord" type connection to a tattoo machine.

As a further non-limiting example, a "clip" or "strut" type adapter 100 can secure the battery to the tattoo machine, while electrical connection is provided though a separate clip cord connection as shown in FIGS. 11, 17, and 18. The clip cord adaptor 100 is attached to the exposed coil and magnet tattoo machine as shown in FIG. 18, and the power supply 15 is then attached to the magnetic connector 104 by insertion into cavity 6 of unit 15. Other modifications and changes, according to design preference, are understood to be within the scope of this disclosure, such as dual wire, single wire (with polarity), balun-type, and so forth. This flexibility gives the exemplary battery system the ability to be attached virtually all the different types of tattoo machines in the industry. And, if configured with a variable power output capability (using the adjustment knob 2), the exemplary battery system can provide an enhanced range of compatibility to various tattoo machines having different voltage requirements. The artist only needs to mount the correct mounting interface adapter for the power connector desired. Or, insert the appropriate power connector into the mounting interface cavity 6. This allows, the exemplary battery system to be easily used with different machine types.

The system is also able to provide different voltages, selectable by the artist. For example, the artist could select from 0-12 volts in increments of 0.01 Volts. The compactness of the exemplary system resulted in a unit weighing less than 1.3 ounces while still providing up to 8 hours of use. Additionally, the display 5 was configured to be turned off (or reduced in brightness) if the display's light was bothersome. Further, the display 5 is configured to be flipped (or rotated) to allow left-handers to easily read it. See FIGS. 22-24.

Figure 19:
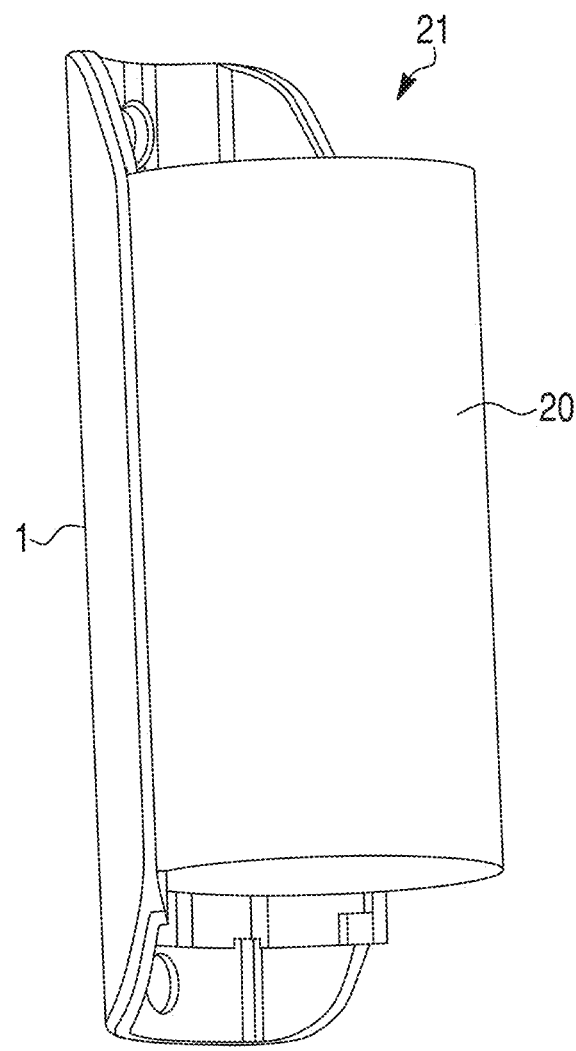
FIG. 19 is a battery pack of the device in FIG. 1.
Figure 20:
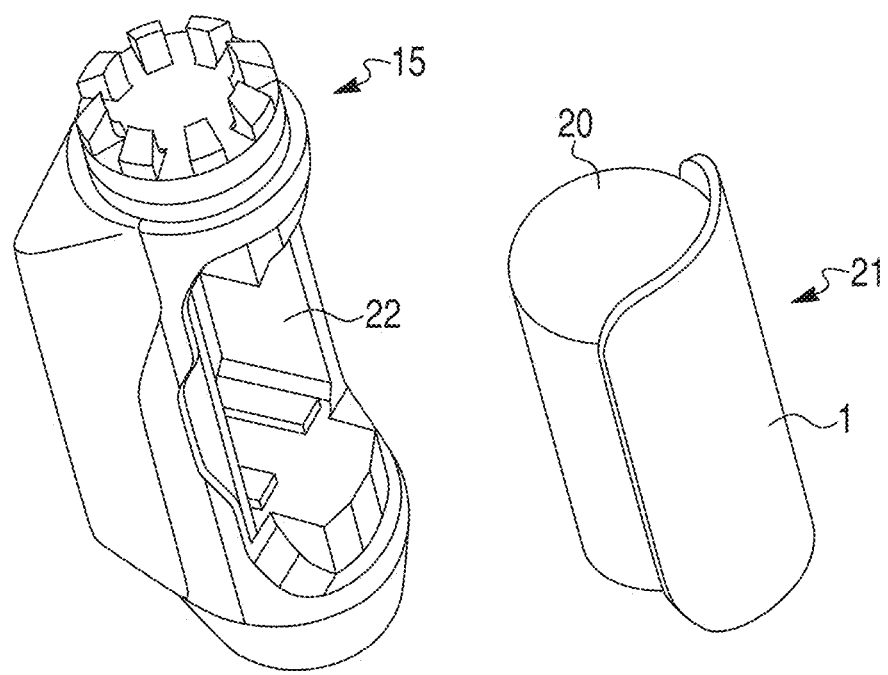
FIG. 20 shows the orientation and insertion of the battery pack of FIG. 19 into the device of FIG. 1.

FIGS. 19 and 20 show the removeable battery cover 1 and affixed battery 20, the battery pack 21, separated from the device housing 15. FIG. 20 shows, particularly, the insertion of the battery pack 21 into the housing battery cavity 22. The battery 20 may comprise cells of a rechargeable lithium ion type totaling, for example, 12-14V, with conventionally known recharging interfaces therefore, i.e., USB, micro USB, etc. The battery can, alternatively, be a generic cell type that can be removed, recharged, and replaced into the internal battery cavity 22 when the battery cavity is equipped to receive such a cell, and the cover 1 for the battery compartment internal cavity 22 operates as just a cover. The removability of the battery either as a unit in combination with the cover, or as a separate cell, eliminates the battery life as the limit on use of the unit 15. Additional batteries or battery packs can be obtained separately thus extending the useful life of the unit 15.

Figure 21:
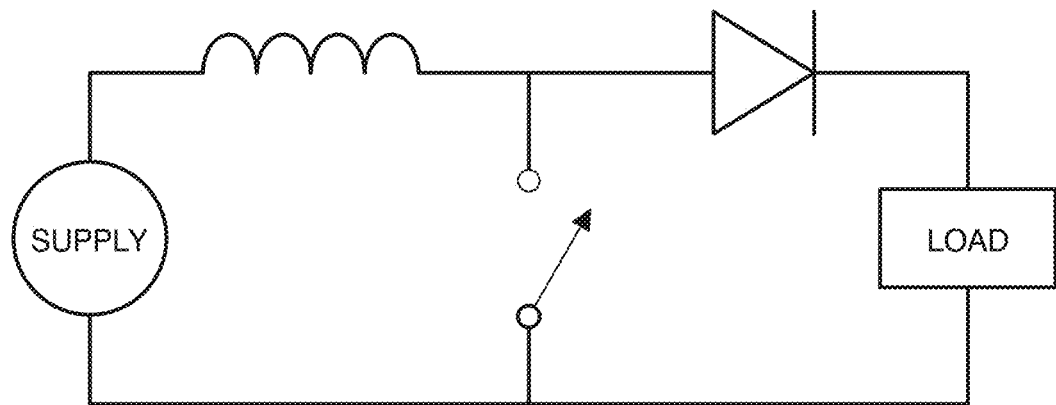
FIG. 21 is a DC-to-DC power converter boost circuit for boosting output voltage of the power supply.

FIG. 21 shows a typical DC-to-DC power boost circuit 110 wherein current is stepped down in exchange for a boost in Voltage. This type of circuit is used to step-up and step down the voltage supply from the battery as the output voltage to the connected tattoo machine and can be used as an alternative to the rotary potentiometer shown in FIG. 2.

We claim:

1. A tattoo device, comprising:
   a tattoo machine;
   a battery housing having a battery and a tattoo machine connection end comprising a mounting interface with a portion that extends away from the battery;
   a display screen;
   an input selector that receives user operational input;
   wherein the mounting interface of the tattoo machine connection end has an internal mounting face and an insertion cavity formed by the portion that extends away from the battery and that receives at least a portion of a tattoo machine electrical connector of the tattoo machine, wherein the internal mounting face electrically couples to the tattoo machine electrical connector to receive a supply of power from the battery in accordance with user input via the input selector; and
   wherein the mounting interface of the tattoo machine connection end provides a magnetic connector that magnetically couples the battery housing to the tattoo machine;
   wherein the display screen and the input selector are located on an exterior surface of the battery housing.

2. The tattoo device of claim 1, wherein the display screen is rotatable.

3. The tattoo device of claim 1, wherein the display screen is selectively arranged between left-handed and right-handed information presentation.

4. The tattoo device of claim 1, wherein the battery is compatible with different tattoo machines.

5. The tattoo device of claim 1, wherein the battery provides a plurality of power outputs.

6. The tattoo device of claim 1, wherein the mounting interface provides a structural connection to the tattoo machine.

7. The tattoo device of claim 1, wherein the mounting interface holds the battery housing to the tattoo machine.

8. The tattoo device of claim 1, wherein the display screen is positioned on the battery housing, and wherein a portion of the battery housing is cylindrical and a portion of the battery housing forms a raised flat section where the display screen is located.

9. The tattoo device of claim 8, wherein the raised flat section comprises angled sides.

10. The tattoo device of claim 1, wherein the display screen is touch sensitive.

11. The tattoo device of claim 1, wherein the display toggles to present a plurality of information.

12. The tattoo device of claim 1, wherein the display screen turns off during use of the tattoo machine.

13. The tattoo device of claim 1, further comprising a mounting interface adapter.

14. A tattoo device, comprising:
    a tattoo machine;
    a battery housing having a battery and a tattoo machine connection end comprising a mounting interface with a portion that extends away from the battery;
    a display screen;
    an input selector that receives user operational input;
    wherein the mounting interface of the tattoo machine connection end has an internal mounting face and an insertion cavity formed by the portion that extends away from the battery and that receives at least a portion of a tattoo machine electrical connector, wherein the internal mounting face electrically couples to the tattoo machine electrical connector to receive a supply of power from the battery in accordance with user input via the input selector;
    wherein the mounting interface of the tattoo machine connection end provides a magnetic connector that magnetically couples the battery housing to the tattoo machine; and
    wherein the mounting interface of the tattoo machine connection end provides a structural connection to the tattoo machine such that the tattoo machine connection end of the battery housing holds the battery housing to the tattoo machine;
    wherein the display screen and the input selector are located on an exterior surface of the battery housing.

15. The tattoo device of claim 14, wherein the display screen is positioned on the battery housing, a portion of the battery housing is cylindrical and a portion of the battery housing forms a raised flat section where the display screen is located.

16. The tattoo device of claim 15, wherein the display screen is rotatable.

17. The tattoo device of claim 15, further comprising a voltage controller that provides voltage in accordance with user operational input via the input selector.

18. The tattoo device of claim 15, further comprising a mounting interface adapter.

19. A tattoo device, comprising:
    a tattoo machine;
    a battery housing having a battery and a tattoo machine connection end comprising a mounting interface with a portion that extends away from the battery;
    a display screen;
    an input selector that receives user operational input;
    a voltage controller that provides an output of the battery;
    wherein the mounting interface of the tattoo machine connection end has an internal mounting face and an insertion cavity formed by the portion that extends away from the battery and that receives at least a portion of a tattoo machine electrical connector of the tattoo machine, wherein the internal mounting face electrically couples to the tattoo machine electrical connector to receive a supply of power from the battery in accordance with the user operational input;
    wherein the mounting interface of the tattoo machine connection end provides a magnetic connector that magnetically couples the battery housing to the tattoo machine;
    wherein the mounting interface of the tattoo machine connection end provides a structural connection to the tattoo machine such that the tattoo machine connection end of the battery housing holds the battery housing to the tattoo machine; and
    wherein a portion of the battery housing is cylindrical and a portion of the battery housing forms a raised flat section where the display screen and the input selector are located.

20. The tattoo device of claim 19, further comprising a mounting interface adapter.

* * * * *